United States Patent
Sarvazyan

(10) Patent No.: US 7,364,696 B1
(45) Date of Patent: Apr. 29, 2008

(54) METHODS AND DEVICES FOR DROPLET MICROCHROMATOGRAPHY

(75) Inventor: Armen P. Sarvazyan, Lambertville, NJ (US)

(73) Assignee: Artann Laboratories, Inc., Lambertville, NJ (US)

( * ) Notice: Subject to any disclaimer, the term of this patent is extended or adjusted under 35 U.S.C. 154(b) by 0 days.

(21) Appl. No.: 11/469,934

(22) Filed: Sep. 5, 2006

Related U.S. Application Data

(63) Continuation-in-part of application No. 10/890,604, filed on Jul. 14, 2004, now abandoned.

(51) Int. Cl.
*B01L 3/00* (2006.01)
*G01N 21/00* (2006.01)

(52) U.S. Cl. .............. 422/61; 435/4; 435/7.1; 435/287.1; 435/287.2; 422/50; 422/57; 73/61.71; 73/61.77

(58) Field of Classification Search ............ 435/4, 435/7.1, 287.1, 287.2; 422/50, 57, 61; 73/61.71, 73/61.77
See application file for complete search history.

(56) References Cited

U.S. PATENT DOCUMENTS

| 6,808,934 | B2 * | 10/2004 | Mutz et al. ............ 506/12 |
| 2002/0168699 | A1 * | 11/2002 | Thompson et al. ...... 435/7.92 |
| 2003/0059849 | A1 * | 3/2003 | Sugahara et al. ........ 435/7.1 |
| 2004/0053340 | A1 * | 3/2004 | De Haard et al. ....... 435/7.2 |
| 2004/0218804 | A1 * | 11/2004 | Affleck et al. .......... 382/141 |

OTHER PUBLICATIONS

Yakhno et al., On the Existence of Regular Structures in Liquid Human Blood Serum (Plasma) and Phase Transitions in the Course of Its Drying, 2003, Technical Physics, vol. 48, No. 4, pp. 23-27.*

* cited by examiner

*Primary Examiner*—Long V. Le
*Assistant Examiner*—Melanie J Yu
(74) *Attorney, Agent, or Firm*—Boris Leschinsky

(57) ABSTRACT

Disclosed devices and methods for droplet microchromatograhy are aimed at optical monitoring and rapid analysis of a drying droplet. The device includes droplet deposition component preferably made as a modified disk adapted to fit in a modified CD disk drive, an optical recorder, and a computer control and image analysis. Recorded timed sequence of images of the process of drying of the droplet is digitally filtered and analyzed using windows selected in each image. Changes of predetermined parameters in each window for each image are calculated to assess temporal and spatial dynamics within the sequence of images reflecting sedimentary pattern formation of a drying droplet. Humidity can be selectively controlled to slow down the drying process allowing "zooming" onto the critical periods of drying of the droplet. Various chemical coatings of the deposition means can be used to enhance the test further. If used with biological fluids, the devices and methods of the invention can provide for rapid diagnosis of a variety of conditions and diseases.

Figure 1:
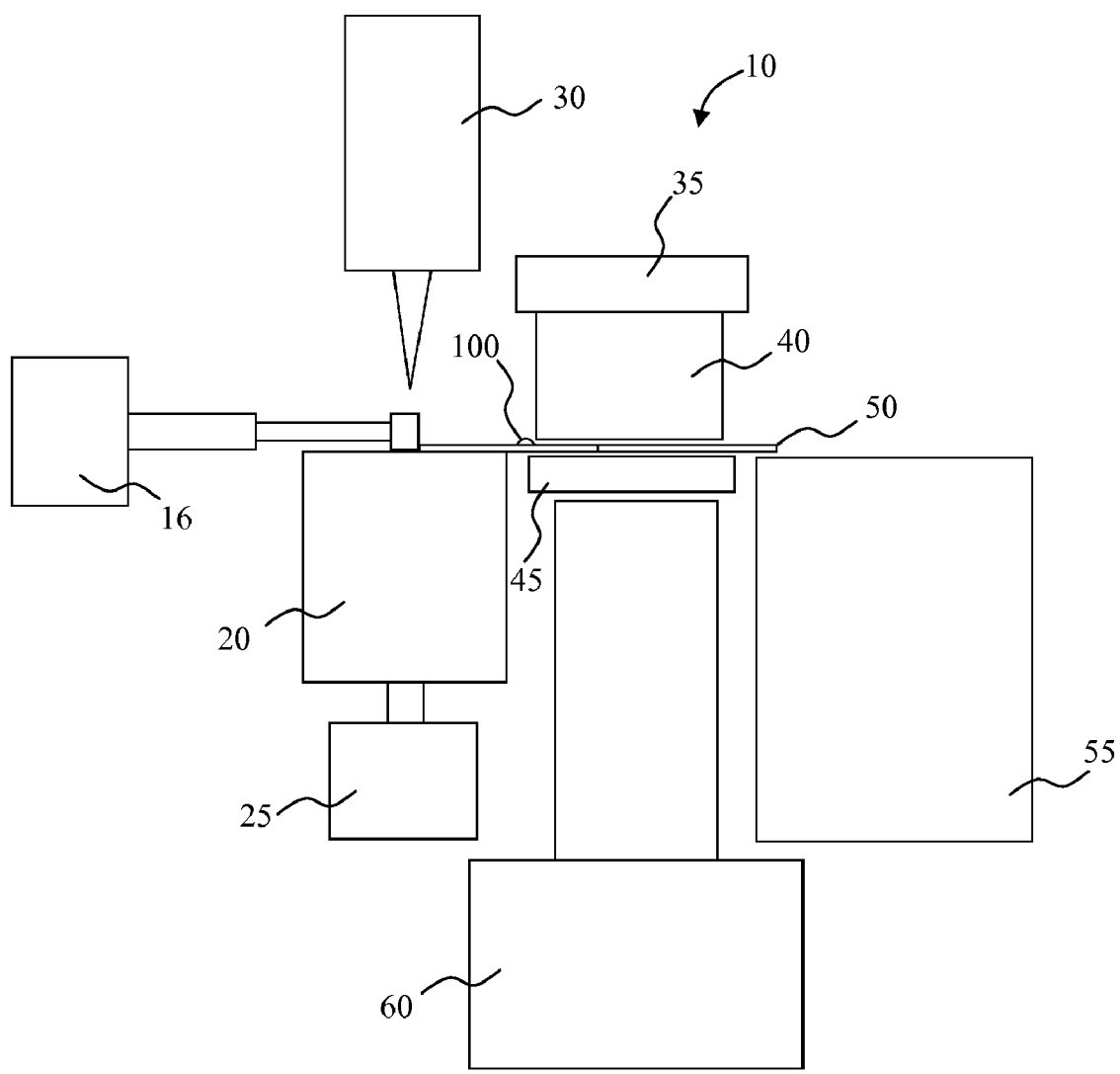

5 Claims, 17 Drawing Sheets

METHODS AND DEVICES FOR DROPLET MICROCHROMATOGRAPHY

CROSS-REFERENCE DATA

This application is a continuation-in-part or a U.S. patent application Ser. No. 10/890,604 filed Jul. 14, 2004 now abandoned entitled METHODS AND DEVICES FOR OPTICAL MONITORING AND RAPID ANALYSIS OF DRYING DROPLETS, which is incorporated herein in its entirety by reference.

BACKGROUND OF THE INVENTION

The present invention relates generally to methods and devices for rapid analysis and determination of composition of multi-component solutions by means of optical monitoring and evaluating the patterns formed during the process of drying of at least one droplet of such solution. More particularly, the invention discloses simple, rapid and sensitive devices for a technique named Droplet MicroChromatography (DMC) designed for assessing various fluids by analyzing the dynamics of sediment pattern formation during the drying of a fluid microdroplet (0.2-10.0 microliter). The proposed approach has a number of unique advantages and in particular it obviates the expense associated with complex proteomic and metabolomic techniques for disease detection which are based on obtaining molecular profiles of bodily fluids.

For the purposes of this description, the word "solution" is used to describe a liquid, which is a product of an act or process by which a solute (whether solid, liquid, or gaseous) is absorbed into and dissolved by a solvent liquid. The solute can be generally regained from the solution by evaporation or drying of a solvent. Suspensions and emulsions are also included in the general category of solutions.

A sub-set of solutions, which is of particular interest for the purposes of the invention, is a category encompassing biological fluids. The term "biological fluid" includes but not limited to the following examples of bodily fluids from animals or humans: blood and blood products such as serum or plasma, saliva, urine, nipple aspirants, synovial fluids, cerebrospinal fluids, sweat, fecal matter, bile, tears, bronchial lavage, swabbings, needle aspirants, semen, vaginal fluids, pre-ejaculate, etc.

The methods of analysis of a solution using the pattern formed by a dried droplet has been known in the prior art for a long time. Initial observations on the potential diagnostic information contained in the patterns formed by dried biological fluids were made over 30 years ago. At the end of the 1960's, the relationship between hormonal changes during the female menstrual cycle and the crystallization of saliva was discovered. Formation of a unique pattern called ferning by a dried droplet of saliva correlates with the fertile period and is related to ovarian function and endocrine activity. Later studies have shown that salivary progesterone concentrations in samples collected by women daily, over extended periods of time, can serve as a means of assessing ovarian function. Based on clinical evidence on the efficacy of detecting a woman's fertile periods by observing characteristic ferning patterns in dried saliva, several US patents were issued on simple optical devices for determining fertile periods. The U.S. Pat. Nos. 4,815,835 by Corona and 5,572,370 by Cho are typical examples of such devices. OvuLook, LLC, a division of TCI Optics, Inc., has developed a commercial device called OvuLook™ and in December of 2001 received FDA clearance for an estrogen based saliva tester that reads ferning patterns.

One of the first attempts to use information contained in the patterns formed by dried biological fluids is presented in the U.S. Pat. No. 4,847,206 issued in 1989 and entitled "Method for the crystal morphological analysis of blood and urine, for early diagnosis and for the production of medicaments". Examples of dried blood patterns corresponding to certain diseases are described, according to experimental data presented in that patent. The samples used for obtaining the patterns shown in that US Patent require a complex and long preparation procedure, which includes many steps such as diluting blood or urine by water, distilling it, calcining the dry cake by heating at a constant rate for a period of 60 to 70 minutes to a temperature of about 600° C., cooling the calcinate for about 2 to 4 hours to a temperature of about 150° C., and several other steps, which altogether make the proposed method hardly practical.

Yakhno et al. conducted extensive studies of various medical and non-medical applications of the drying droplet approach. Results of their studies are summarized in the PCT application No. WO 02/059595 incorporated herein by reference in its entirety and other publications. The major focus on their studies was not the analysis of formed patterns but measurements of "acousto-mechanical impedance" (AMI) of the oscillating quartz on which the droplet of a tested liquid was drying. Several applications of the method were explored, such as quality control of beverages and liquid foods, detection of odors by measuring solutions through which "scented" air was bubbled, and medical diagnostics based on measurements of temporal changes of AMI in the course of drying of a droplet of biological fluids: blood plasma, urine and saliva.

Yakhno reported various potential diagnostic applications of acoustical monitoring of the droplet drying process. It was demonstrated that the drying dynamics of a droplet of blood plasma from a pregnant woman with normal pregnancy differs significantly from that of women at risk for spontaneous abortion. It was also shown that the dynamics of blood serum droplet drying is different for patients with breast cancer and healthy women. The patterns for cancer patients have distinct characteristic features different from those for healthy women, such as larger structural elements and well-defined linear formations. Difference in the patterns for two types of cancer is also quite obvious. Pregnancy results in characteristic patterns. Moreover, there is a clear difference in the patterns for the in-time versus pre-term delivery.

Another example of using the patterns formed by the dried biological fluid droplet is described in the Russian Patents No. 2,127,430 by Buzoverja et al and 2,007,716 by Shabalin et al. The sample of fluid is dried and then the so-called "crystallogram" or pattern is analyzed for the presence of pathological markers.

A general process of determining the biological state through discovery and analysis of hidden biological data is described in the US Patent Application No. 2003/0004402 by Hitt et al. incorporated herein by reference in its entirety. The methods described in this patent application concern processing large volumes of data related to a biological fluid. This patent indirectly provides some useful background information for some aspects of the method of the present invention. More specifically, the use of databases for comparison with the patient's sample as well as neural network based learning systems are described in the patent and may be used for some aspects of the method of the present invention.

This and other methods have a disadvantage of having only the final pattern of the dried droplet available for analysis. There is no mentioning in the prior art of analyzing the temporal and spatial dynamics of structural changes in the sequence of patterns formed by the sediment in the drying droplet although the multitude and sequence of patterns formed and the time intervals between formation of certain patterns can yield substantial information about the composition of the solution.

The need therefore exists for such methods and devices that allow the optical monitoring and analysis of the composition of a solution based on the dynamics of drying of a droplet of such solution.

SUMMARY OF THE INVENTION

Accordingly, it is an object of the present invention to overcome these and other drawbacks of the prior art by providing novel method and devices for droplet microchromotography or optical monitoring of changes of the patterns formed by drying droplet to provide a rapid analysis of a solution.

It is another object of the present invention to provide diagnostic methods and devices for determining a biological state of an organism based on analyzing the dynamics of pattern formation of a biological fluid.

It is a further object of the present invention to provide enhancement for diagnostic methods and devices by using slides with different target agent coatings specifically interacting with the components of the droplet of a solution and optically monitoring the pattern formation sequence while drying that droplet thereafter. In a further object of the invention, disk drive means and modified disposable disks are provided to facilitate the use of the methods of the invention.

It is yet a further object of the present invention to provide methods and devices for detecting changes in pattern sequence of a droplet of a biological fluid indicating the presence of a disease state (such as cancer for example) as well as monitoring the progress of treatment thereof. In a related further object of the invention, simultaneous analysis of pattern formation at various parts of the droplet is used to obtain useful information as to its molecular content.

It is yet a further object of the present invention to provide methods and devices for detecting such disease as well as monitoring the progress of treatment thereof at a location other than a medical office such as at the patient's home, work, recreation, or another remote place.

It is yet another object of the invention to provide methods and devices for detecting specific agents by analyzing differences in the pattern formation dynamics at different rates of drying of a droplet of a solution including a biological fluid.

Droplet MicroChromatography of the present invention may be viewed as a branch of chromatography, which provides separation of the molecular components of the analyzed liquid both in time and space. However, there is a principal difference between conventional liquid chromatography and the proposed methods and devices of the invention. In DMC, the spatial and temporal separation of molecular components occurs through a series of highly cooperative phase transitions. DMC takes advantage of the evaporation of solvent from the tested sample—a process which is generally considered undesirable, and a significant technical hurdle, in many other analytical technologies described in the prior art. In the process of droplet desiccation, the concentration of various solutes sequentially reaches, and then exceeds, the limit of solubility. As a result, sediment formation resembles a series of "avalanches," separating certain molecular components of the fluid in time and space. This highly cooperative process is sensitive to molecular composition and intermolecular interactions in the fluid. It can depend significantly on certain minor components, which act as triggers in aggregation and patterning of major components. This phenomenon provides extensive possibilities for enhancing the manifestation of those molecular components of the tested fluid that are indicative of a disease or physiological condition. By adding certain ligands to the tested fluid, or by coating the deposition slide by various agents, e.g. antibodies, it might be possible to selectively amplify the sensitivity of the drying droplet test towards a chosen component of the fluid. The versatility imparted to DMC by the use of interchangeable, disposable deposition slides with a nearly endless variety of possible coatings permits, within one device, both nonspecific and specific recognition of analytes. The specific sensitivity of the technique can also be enhanced by manipulating the drying conditions, since the structures formed by crystallization processes can be highly dependent on desiccation rate. By slowing down the rate of droplet drying, it is possible to "zoom" to that stage of pattern formation at which the contribution of a component of interest is most pronounced.

Among the components of the droplet of many biological fluids are many molecules with surfactant properties which, during a fast drying process, create steep gradients of surface tension. These gradients result in vigorous microstreaming and convection within the volume of the droplet. While desiccation causes the concentration of each solute to increase, the microstreaming and convection ensure efficient stirring and mixing so that the distribution of each component remains uniform within most of the volume of the droplet. This stirring is greatly impaired near the junction between the droplet edge and the solid substrate. Consequently, the concentration of a particular component near this junction reaches a supersaturated level earlier than in other parts of the droplet. Initial precipitation of the supersaturated component starts at the droplet edge, forming the outer ring of the drying droplet pattern. The time dependence and position of the sequential phase transitions form a complex pattern of rings of precipitated material characteristic of the composition of the bodily fluid.

In blood serum for example, which has high protein concentrations, the outer rings of the pattern comprise primarily proteins, with small organic molecules and inorganic salts depositing to form the central regions of the patterns. Macromolecules interact with each other, with small molecules, and with the substrate surface. Any and all of these interactions may influence the deposit pattern. In addition to direct associations with macromolecules, small organic molecules and inorganic salts influence the deposit pattern in a number of ways. As solvent is removed from the droplet, the ionic strength of the solution increases and the dielectric constant decreases, thus altering the strength of electrostatic interactions among the solution components.

Figure 10:
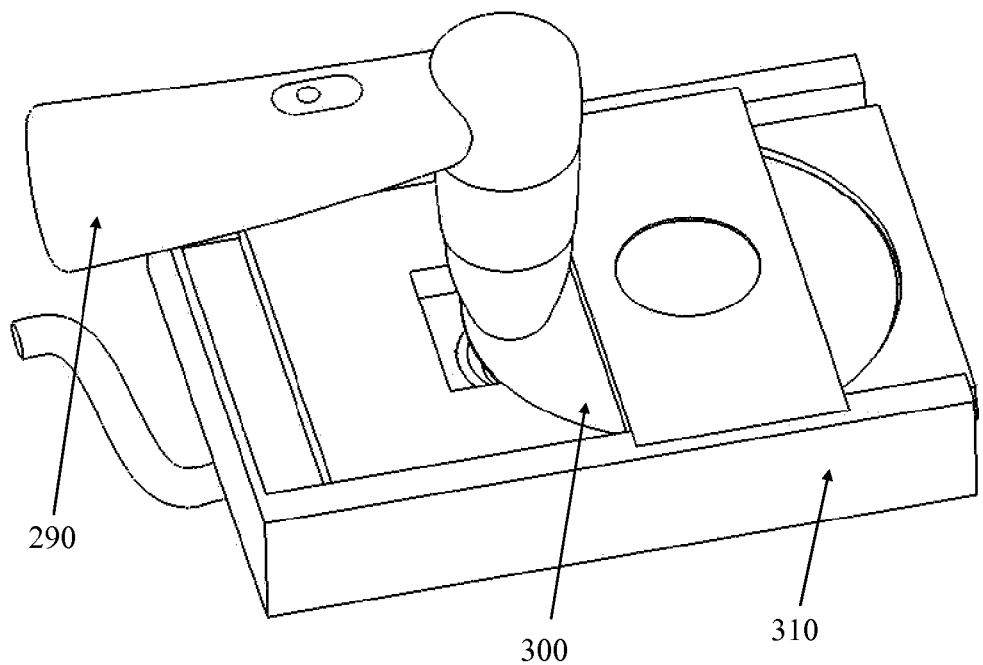
Figure 11:
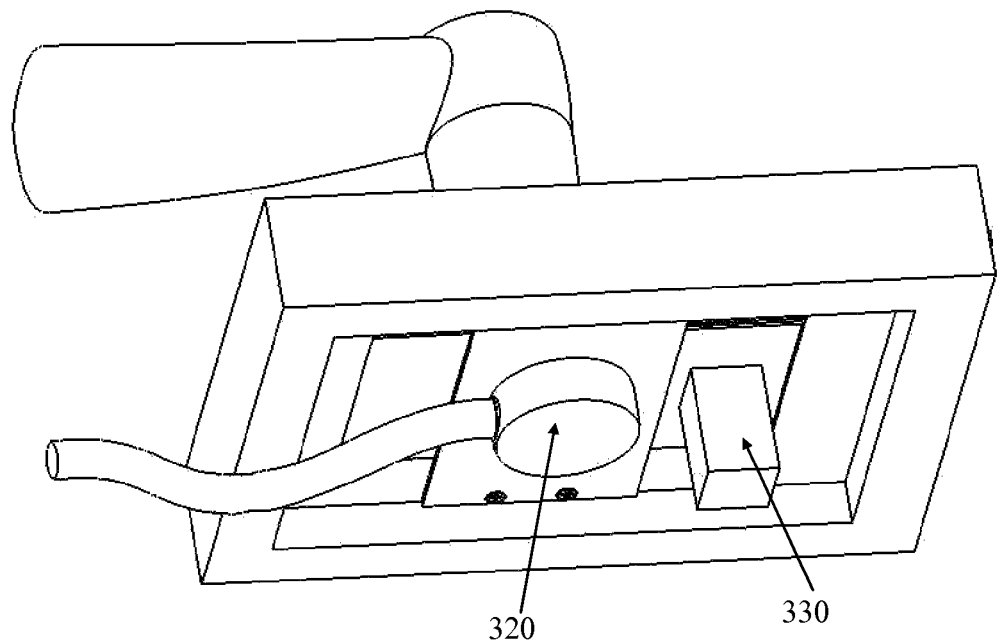
Figure 12:
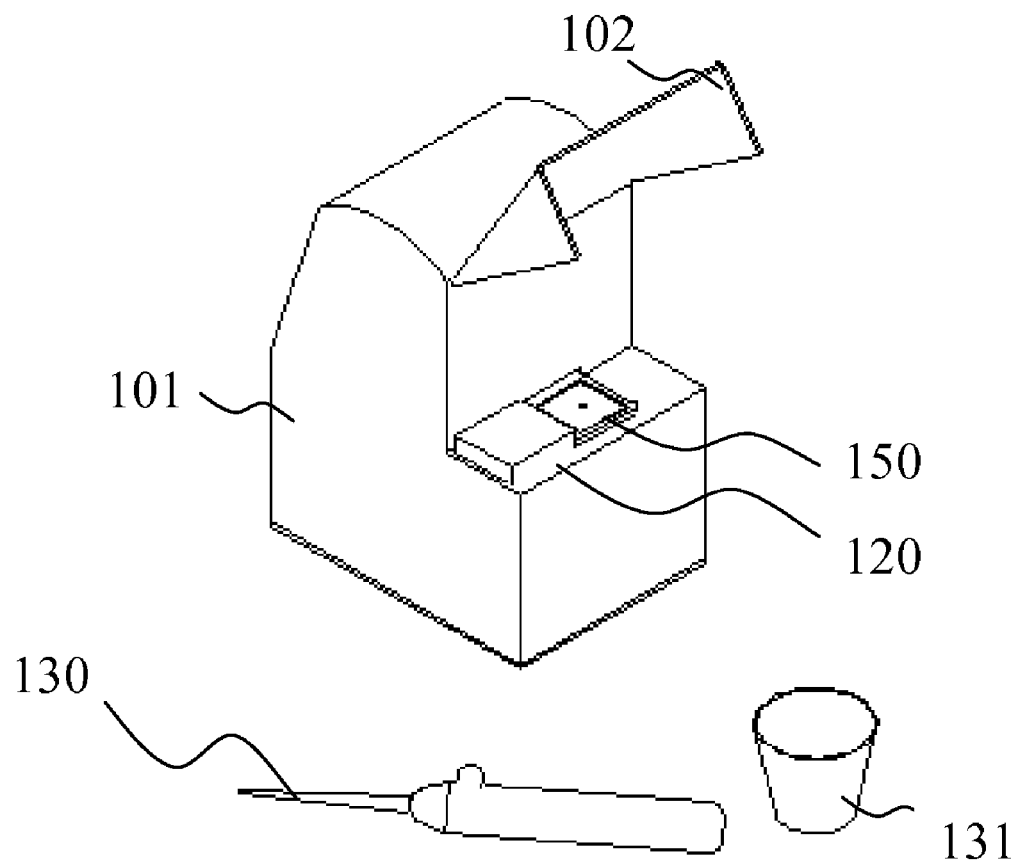
Figure 13:
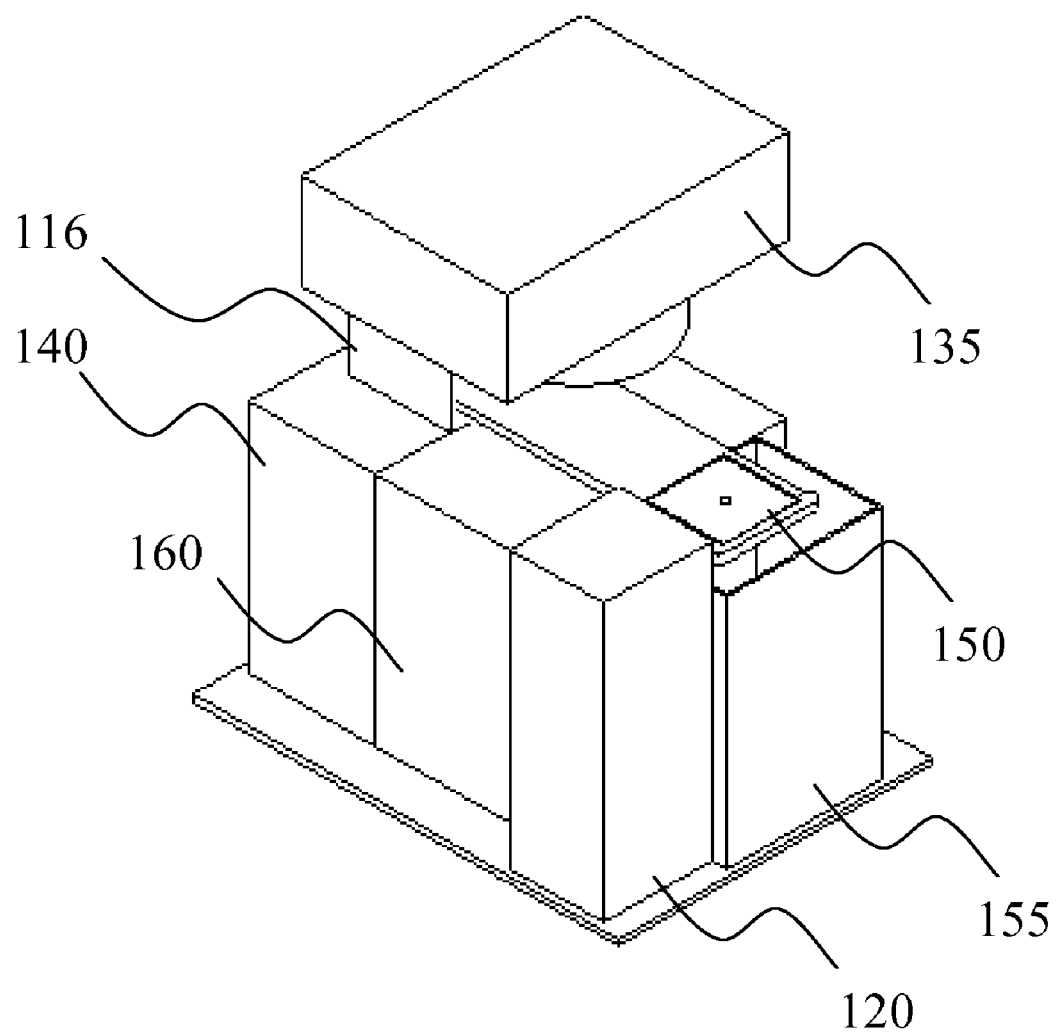
Figure 14:
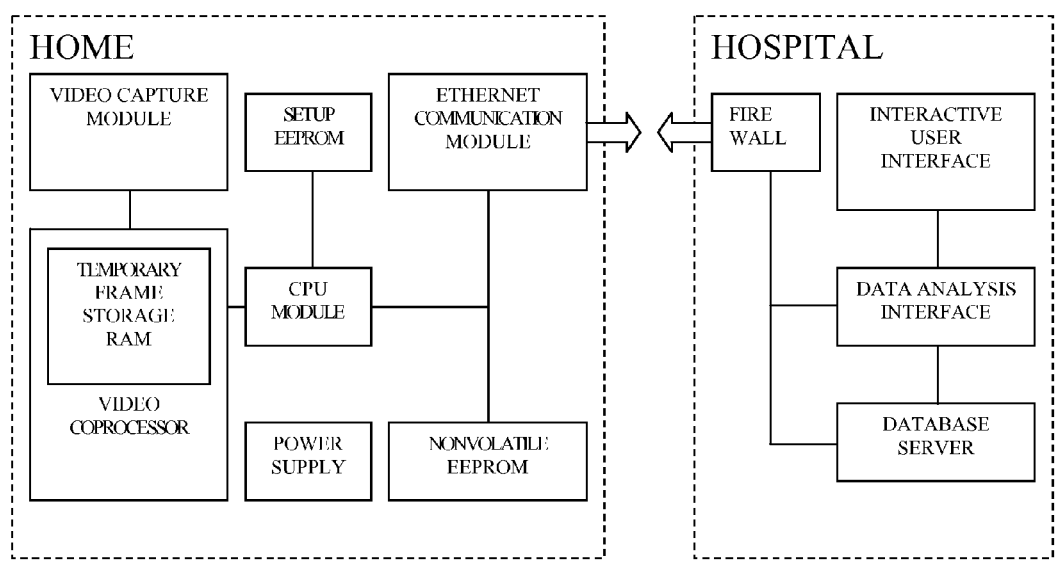
Figure 15:
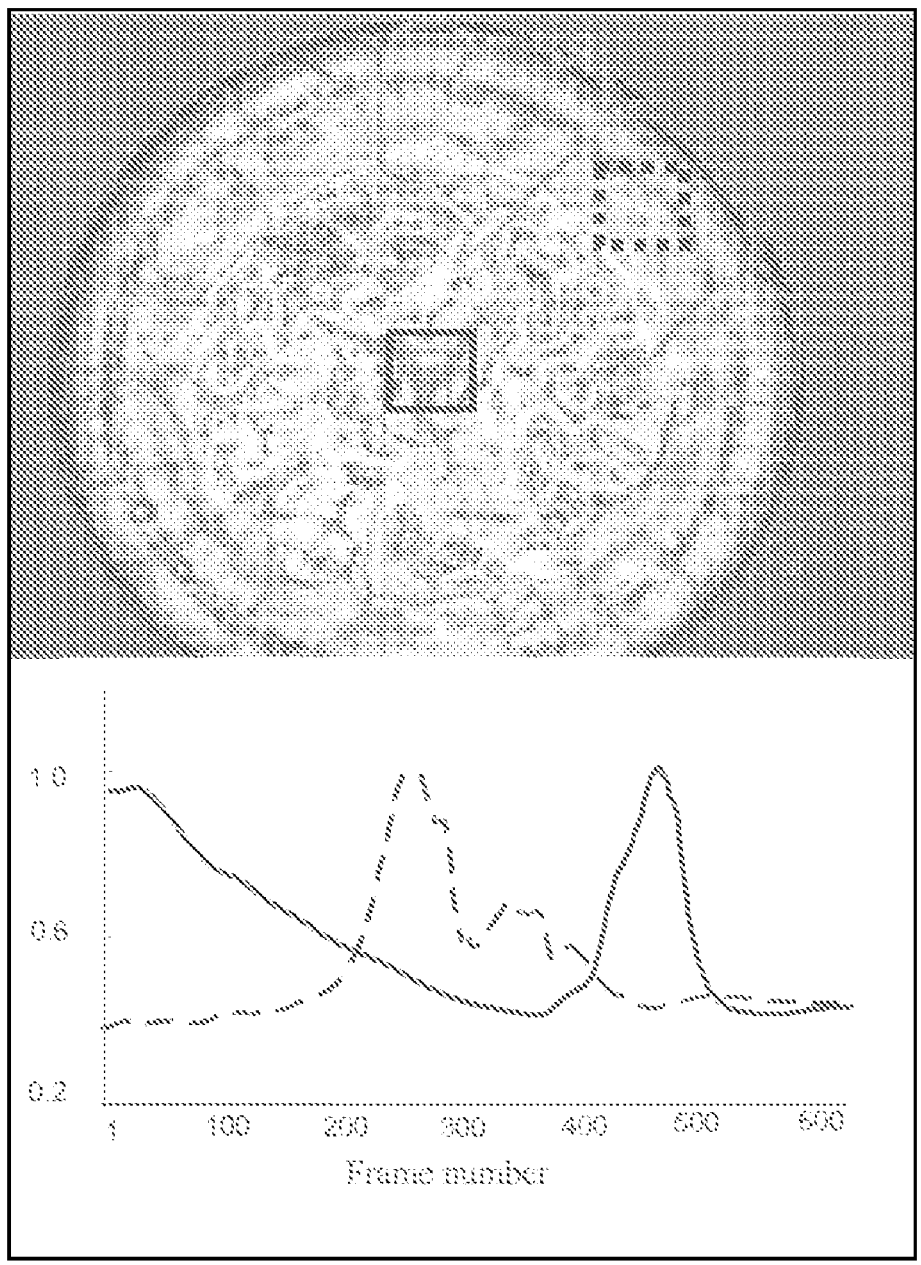
Figure 16:
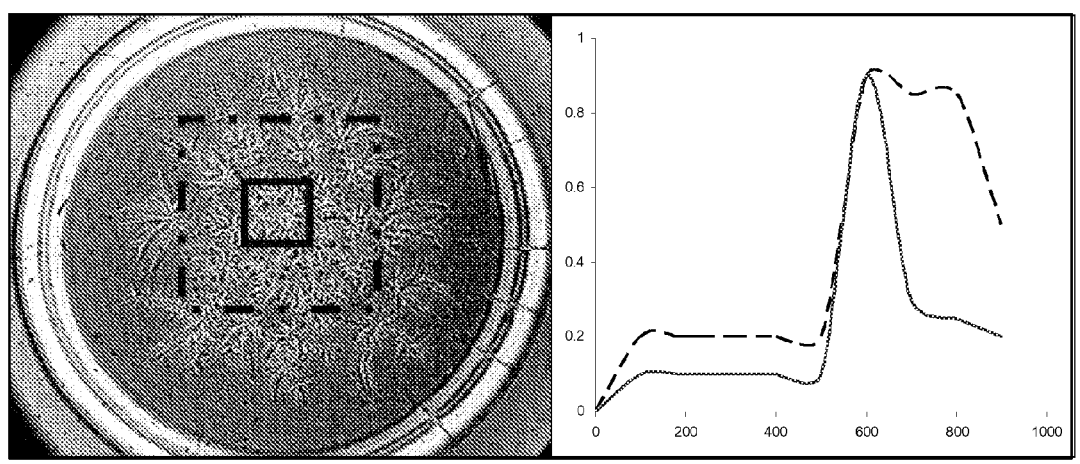
Figure 17:
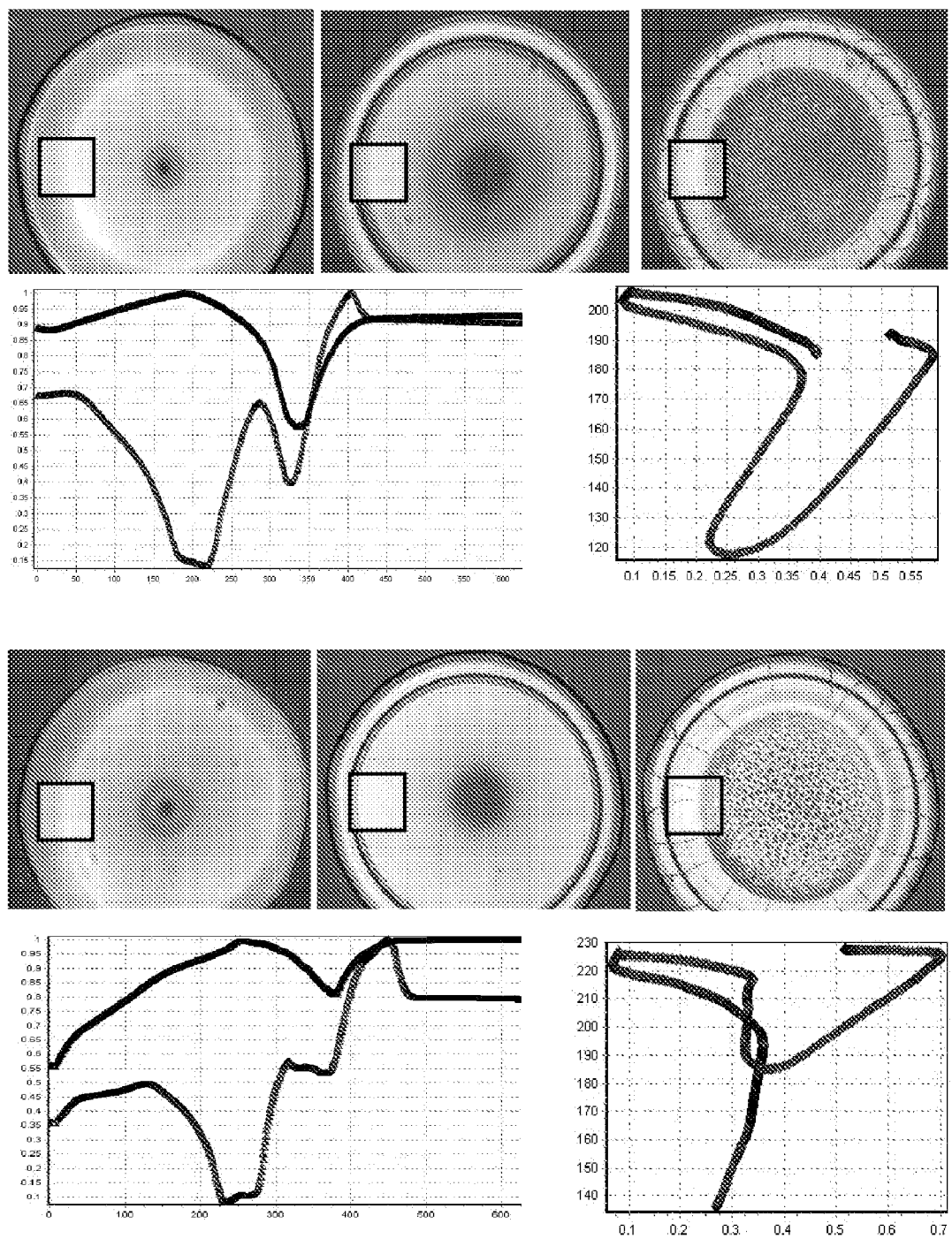
Figure 18:
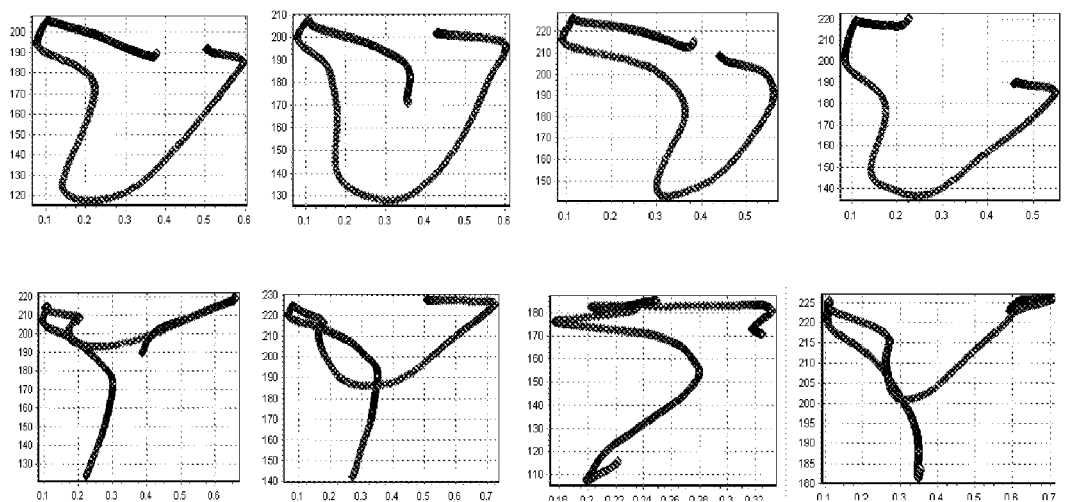
Figure 19:
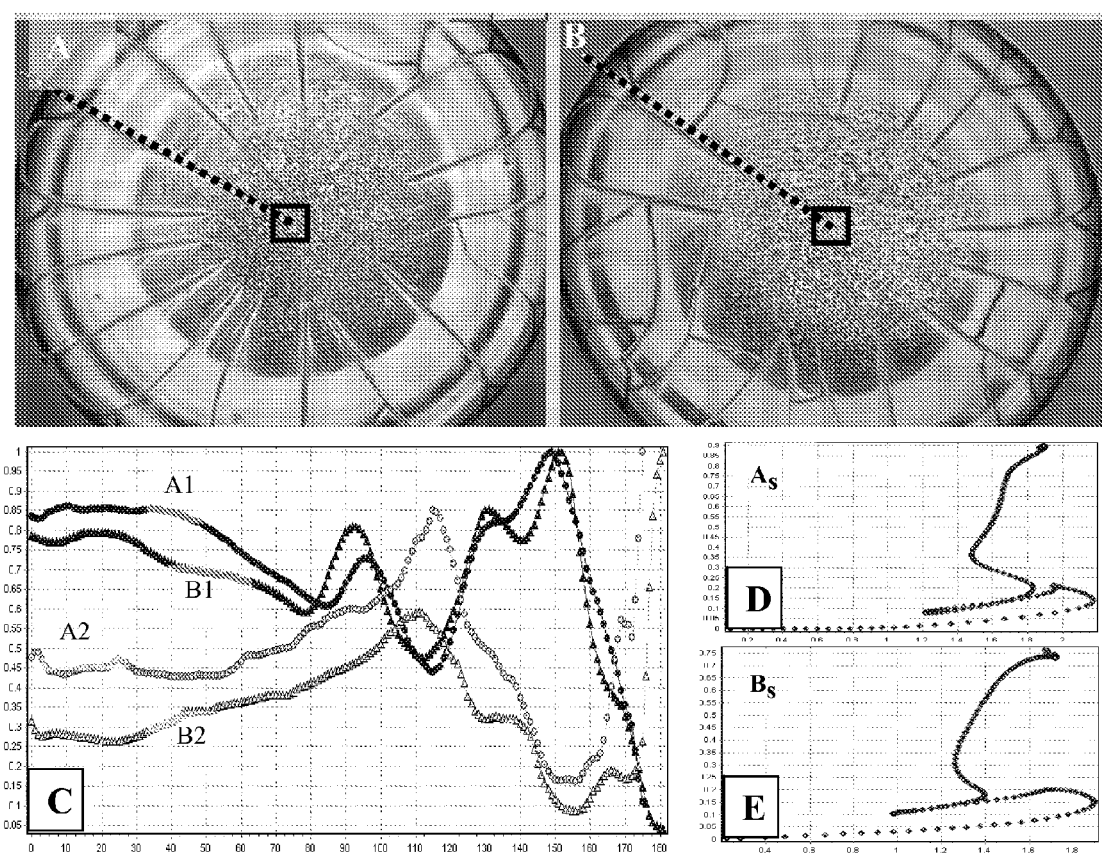

The present invention encompasses methods of determination of a multi-component fluid composition by analyzing the time and location of patterns formed during drying of a droplet of said fluid. More specifically, the present invention encompasses methods of assessing biological fluids and diagnosing diseases by recording the dynamics of said pattern formation and relating said dynamics to the global database on corresponding biological fluid pattern dynamics. The invention further encompasses methods of detecting chemical and biological agents by analyzing the sequence of patterns formed by drying droplets of solutions of substances selectively interacting with the surface of the slide coated by various target agent coatings. The invention also encompasses methods of detecting changes in the dynamics of drying droplets of biological fluids for the diagnosis of diseases, such as cancer and pathogen infections. The invention further encompasses methods of analyzing specific changes in the dynamics of drying droplets of biological fluids for the monitoring of treatment of diseases. The present invention also encompasses methods of detecting specific agents by analyzing differences in the pattern dynamics at different rates of droplet drying. The invention further encompasses methods of detecting changes in the dynamics of drying droplets of fluids in industrial processes such as food and drug manufacturing such as for the purposes of controlling or monitoring the purity, quality, or other desirable characteristics of the fluid.

The invention further describes devices for recording and analyzing the dynamics of the drying droplet pattern. In its most basic form, such device includes a droplet deposition means, an optical recording means for obtaining a sequence of patterns formed by at least one drying droplet and transforming them into a form suitable for further analysis, and a computer control and analysis system to analyze the images and provide the output result.

In practical terms, the device of the present invention in its most basic form includes a simple deposition plate such as a glass or quartz plate or slide serving as a droplet deposition means. Calibrated droplet deposition devices well known in general in the prior art can also be used effectively as more sophisticated droplet deposition means as will be described in more detail below. Advantageously, deposition plates with various coatings containing target agents can be used to enhance the sensitivity of the analysis of the present invention. In a preferred embodiment, a disposable disk similar in size to a standard computer compact disk (CD) with a number of coated and uncoated surfaces can be used as a droplet deposition means. Such disk can be adapted to be used with a modified disk drive to make a simple and reliable device for DMC.

A simple video camera mounted to record the formation of drying patterns would serve as an example of the most basic optical recording means for the system of the present invention. Better yet, a CCD camera connected to a computer would provide the data stream input needed for further analysis of the solution. Other more sophisticated optical recording means and droplet deposition means are described in greater detail below.

In a preferred embodiment of the device, a disk-drive with means to control humidity is used to conduct the evaluation a droplet deposited over a disk as described in more detail below.

In general, the major aspects of the present invention are as listed below:

- Digitally recoding temporal evolution of the pattern formed by a drying droplet of a fluid including bodily fluids, and relating measurement data to diagnostically relevant changes in the composition of the fluid;
- Enhancing the sensitivity of the method to a particular target agent by the use of a variety of coatings of the deposition slide, or by optically labeling the target agent;
- "Zooming" to a specific concentration range at which a particular molecular interaction or process of interest is most pronounced by slowing down of the droplet drying rate;
- Proposing methods and algorithms for obtaining diagnostic information from the DMC data by calculating characteristic "signature" of the measured liquid;
- Designing a device based on the modified computer disk drive for standardized monitoring of droplet deposition and drying with computerized control of temperature and humidity and with disposable CD-based slides having sections of coated and uncoated surfaces providing a possibility to make measurements of droplets of one fluid on several coatings in one experiment.

DMC technology is aimed at becoming a platform for an array of easy-to-use and low cost specialized devices for assessment of bodily fluids for diagnostic purposes. This simple, inexpensive, and sensitive test can give researchers immediate feedback on disease progression or regression. The technology also has a potential use in guided therapy when drug dosage relies on a sensitive test that shows the effectiveness of treatment.

There are potential clinical applications of DMC in both larger and smaller office-based laboratories. The larger laboratories will benefit from the capability of providing more rapid testing services than are currently available. The smaller laboratories will benefit by providing a more complete array of testing services without a large capital outlay. For the majority of the population, primary care is the main point of entry into the health care system. Community-based primary care practice settings, primary care practice-based research networks or similar organizational structures for delivering and evaluating primary care may be well-suited to use DMC technology. The portability inherent to DMC makes it a good candidate for broad screening for a variety of diseases in low income populations, rural areas, small hospitals and even at home.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 1 is a diagram of the first embodiment of the invention showing optical recording means located underneath the droplet deposition means, FIG. 2 is a diagram of the second embodiment of the invention showing the optical recording means located above the droplet deposition means, FIG. 3 is a schematic drawing of the third embodiment of the invention showing film means for droplet deposition with one or more droplets in parallel being analyzed by the optical recording means, FIG. 4 is a schematic drawing of the fourth embodiment of the invention showing multi-lane film, each lane is coated by a different target agent for enhancing the test sensitivity, FIG. 5 is a schematic drawing of the fifth embodiment of the invention showing a multi-tip pipette for simultaneous processing of multiple samples at the same time, FIG. 6 is a diagram of the sixth embodiment of the invention showing two-channel pipette means, FIG. 7 is a diagram of the seventh embodiment of the invention showing inverted droplet deposition means to allow for droplet drying in inverted position, FIG. 8 is a general view of the eighth and most preferred embodiment of the invention using a disk drive, FIG. 9 is a top view of the device shown on FIG. 8, FIG. 10 is a top view of the disk drive and microscope means of the device shown on FIG. 8, FIG. 11 is a view from the bottom of the same portion of the device as shown on FIG. 10, FIG. 12 illustrates a general view of the home based version of the diagnostic devices according to the present invention, FIG. 13 shows a schematic diagram of the device shown on FIG. 12, FIG. 14 shows an electrical diagram of the device shown on FIG. 12 and its interaction with a remote hospital image analysis device, FIG. 15 shows an example of time dependent difference in intensity graphs taken at two windows located at different points on an image of a drying droplet, FIG. 16 shows the difference in the intensity graphs of a window when its size is varied, FIG. 17 shows a comparison of pattern signatures for healthy and myeloma patient, FIG. 18 shows the reproducibility of signatures for healthy and myeloma patient, and finally FIG. 19 shows an example of characterization of a serum sample based on a final image in a sequence of images.

DETAILED DESCRIPTION OF THE FIRST PREFERRED EMBODIMENT OF THE INVENTION

A detailed description of the present invention follows with reference to accompanying drawings in which like elements are indicated by like reference letters and numerals.

The first embodiment is shown schematically on FIG. 1 and includes a droplet deposition means 10 with an optical recording means 60 and a computer control and image analysis means (not shown). The droplet deposition means 10 in turn comprises a pipette 30 adapted to deposit predefined volumes of solution as a droplet 100 onto a deposition plate means 50 supplied by a slide feed 16. Examples of a deposition plate include glass or quartz plate, slide, or cassette supplied from the glass cassette compartment 20 supported optionally by a glass separator 25 or from another appropriate source. The device of the invention includes further provisions to position the droplet on a deposition plate means 50 onto a sample holder 45 inside an optional climate controlled chamber 40 and illuminate it by a light source 35.

In a preferred embodiment, the light source 35 provides diffused polychrome light, which permits achieving best discrimination between colored structures of the droplet. Preferably, blue, green, and red LED diodes with three channels of electrical current control are used as a light source 35.

Optical recording means include in this case a digital microscope 60. Alternatively, a CCD camera can also be used such as for example a Pixera 120es Pro color scientific grade CCD camera attached to a long focal distance zoom lens such as Navitar. In this embodiment, the optical recording means are mounted underneath the droplet and observe the drying sequence from the bottom through a clear deposition plate.

The computer control and image analysis means generally consists of a data collecting means connected to the optical recording means such as a digital microscope and adapted to receive the stream of data containing the timed sequence of images of the drying droplet. Once collected, the images are then analyzed to look for specific patterns and specific timed of formation thereof and the results are then provided. The details of the image processing and analysis are described below in greater detail. One important aspect of the computer control and image analysis means though is the ability to recognize the end of the drying cycle so the system is capable of advancing the droplet deposition means to the new one and discard the old one automatically. Alternatively, the duration of the drying cycle is set for a predetermined time.

After completion of the data collection, the droplet and the deposition plate are discarded into a glass collector 55.

DETAILED DESCRIPTION OF THE SECOND PREFERRED EMBODIMENT OF THE INVENTION

Figure 2:
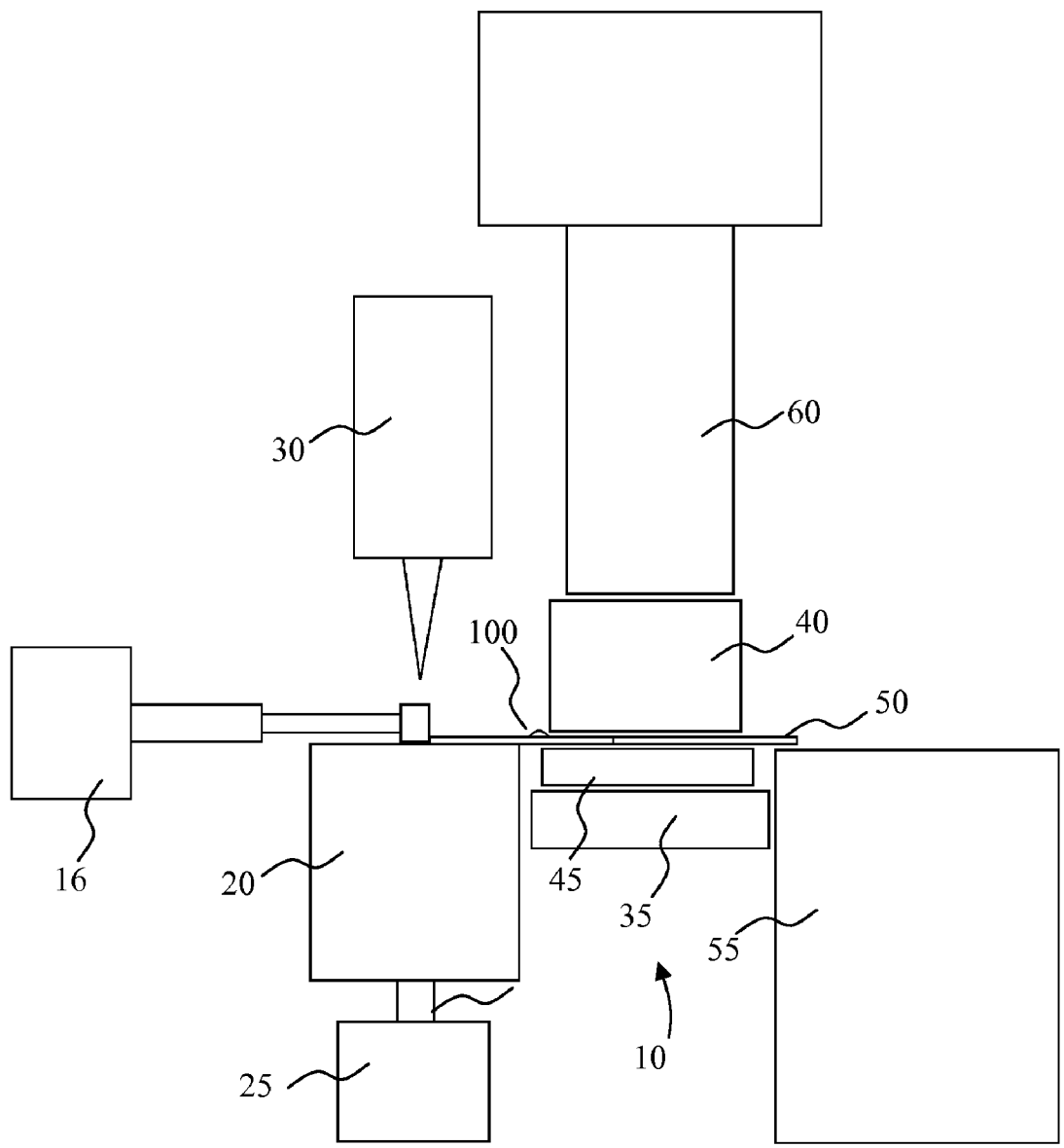

The block-diagram of the second embodiment of the present invention is shown on FIG. 2 including all the same elements as the first embodiment but in a different orientation. In particular, the optical recording means 60 is located above the climate control chamber 40 and observes the drying droplet from the top. The droplet in that case may be deposited on any suitable deposition plate, which does not have to be optically transparent.

Observing the droplet from the top or the bottom or optionally from both sides simultaneously (not shown on the drawings) reveals various details of the dynamics of the drying process.

DETAILED DESCRIPTION OF THE THIRD PREFERRED EMBODIMENT OF THE INVENTION

Figure 3:
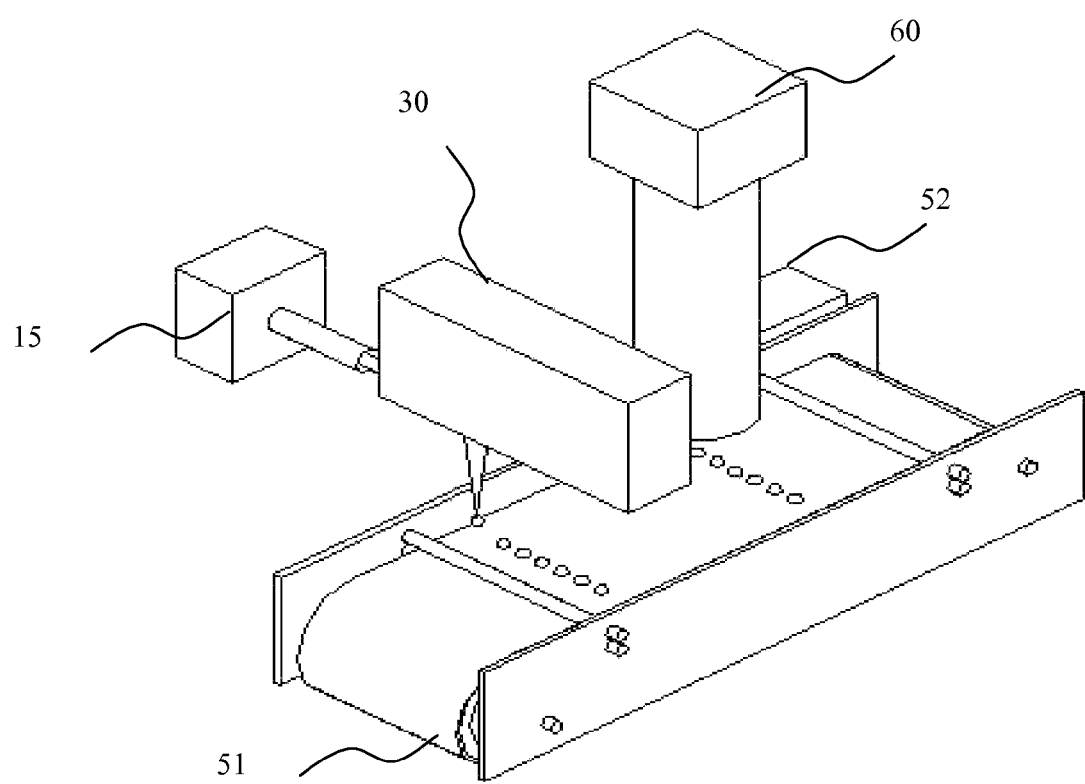

The schematic depiction of the third embodiment of the present invention is shown on FIG. 3 including an optional solution feed device 15 to supply the pipette means 30 and a different droplet deposition plate means, namely a film 51, which accepts one or more deposited droplets in parallel. The film is advanced from one roller over to another via a film advancing means 52 such as a stepper motor for example. The motor is controlled so that the advancement of the film is started and stopped in such a way that the droplet is positioned under the optical recording means 60 for a sufficient time for drying to occur and data collection to proceed without moving the droplet. Once the data is collected, the film is advanced to that a fresh sample is positioned in the field of view of the optical recording means. Used droplets are discarded with the used roll of film.

Optional provisions are contemplated for adjustment means to position the optical recording means 60 at various points across the width of the film so as to allow more samples to be processed per unit of length of the film.

Additionally, the optical recording means may have optional provisions to record the drying sequence and pattern forming of more than one droplet at a time. Further data processing step should in this case be capable of recognizing that fact and separate data from more than one droplet.

DETAILED DESCRIPTION OF THE FOURTH PREFERRED EMBODIMENT OF THE INVENTION

The fourth embodiment of the present invention includes provisions to record the drying of a droplet deposited onto deposition plate or film coated with a compound selectively interacting with certain components of the tested solution. Such compound may be of different nature but the general purpose of such coating is to increase the sensitivity of the test by modifying the drying process dynamics following specific interaction between components of the solution of interest and the coating compound.

Figure 4:
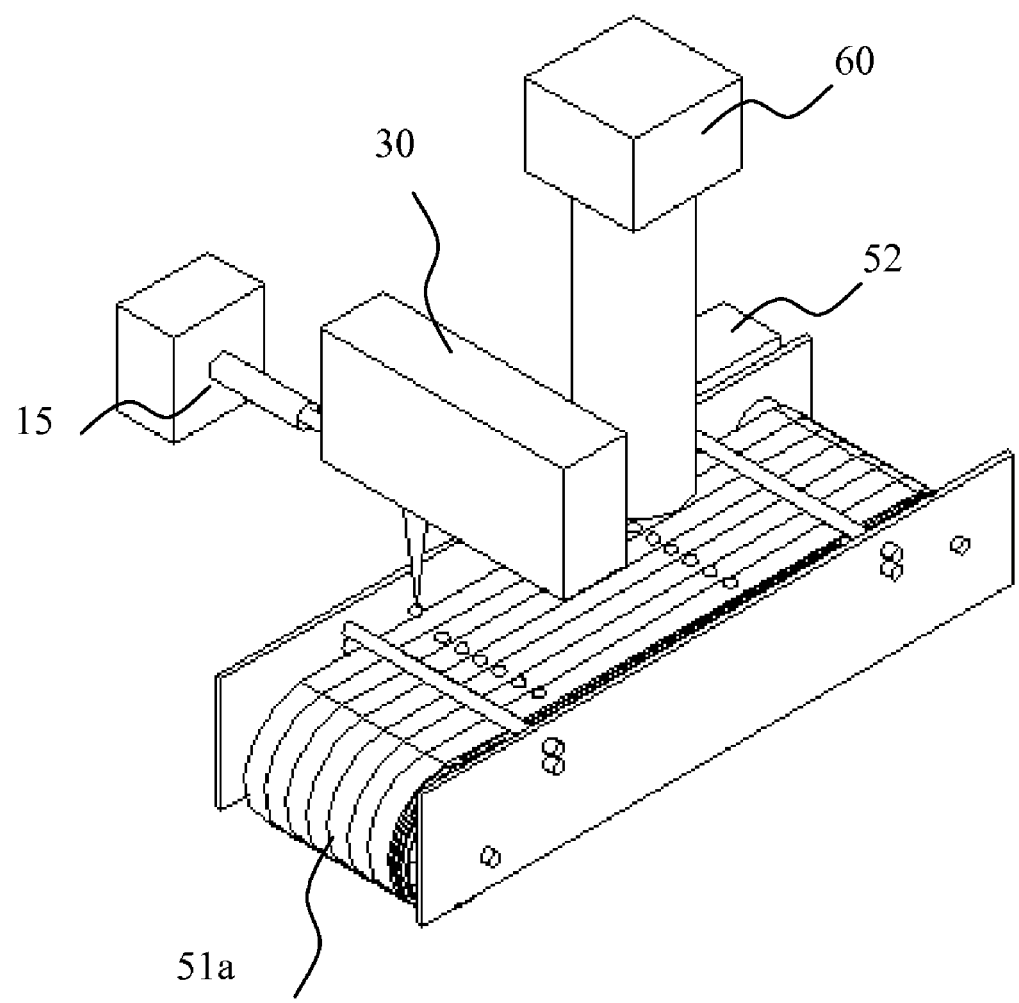

In a further advancement of this concept, FIG. 4 shows the deposition film coated with more than one compounds and forming deposition lanes on the film 51a. It is envisioned that the pipette means 30 may be capable of depositing one droplet at a time or more than one including depositing droplets in parallel to all lanes on the deposition film or plate. Optical recording means 60 are also capable of recording the drying patterns of one or more droplets in parallel therefore the speed and statistical significance of testing is increased further while its sensitivity is enhanced by the target agents.

Various coating compounds may be used for the purposes of the invention. The methods of the invention include detecting a specific solute in the tested liquid droplet by drying it on a surface coated by a selected reagent or a compound, which interacts specifically by macromolecule-to-macromolecule action. These macromolecules may be any combination of protein (including antibody), nucleic acid, carbohydrate, or synthetic polymer; macromolecule-to-small molecule interactions; or small molecule-to-small molecule interactions; or interactions that are non-specific via charge-to-charge; or hydrophobic interactions; or other nonspecific surface effects. Antibodies included in a coating may allow detecting of specific proteins or other components of a solution.

The present invention also encompasses methods of detecting specific compounds by analyzing differences in the pattern dynamics of droplet drying as a function of the following preferred groups of specific compounds:

salts such as for example ammonium sulfate;
detergents and surfactants for example dodecyl sulfate or lauryl sulfate and various cationic detergents such as cetyl (or hexadecyl)-trimethyl ammonium bromide, dimethyldioctadecylammonium bromide, dioleyldimethylammonium chloride, and 1,2-dioleyl-3-N,N,N-trimethylaminopropane chloride;
cosolvents especially those that are miscible with water, such as ethanol, isopropanol, and dimethyl sulfoxide;
charged or neutral polymers such as for example polyethylene glycol or polypropylene glycol;
specific agents in a liquid containing an optical marker that interacts or binds specifically to the target agent; and
denaturants.

DETAILED DESCRIPTION OF THE FIFTH PREFERRED EMBODIMENT OF THE INVENTION

Figure 5:
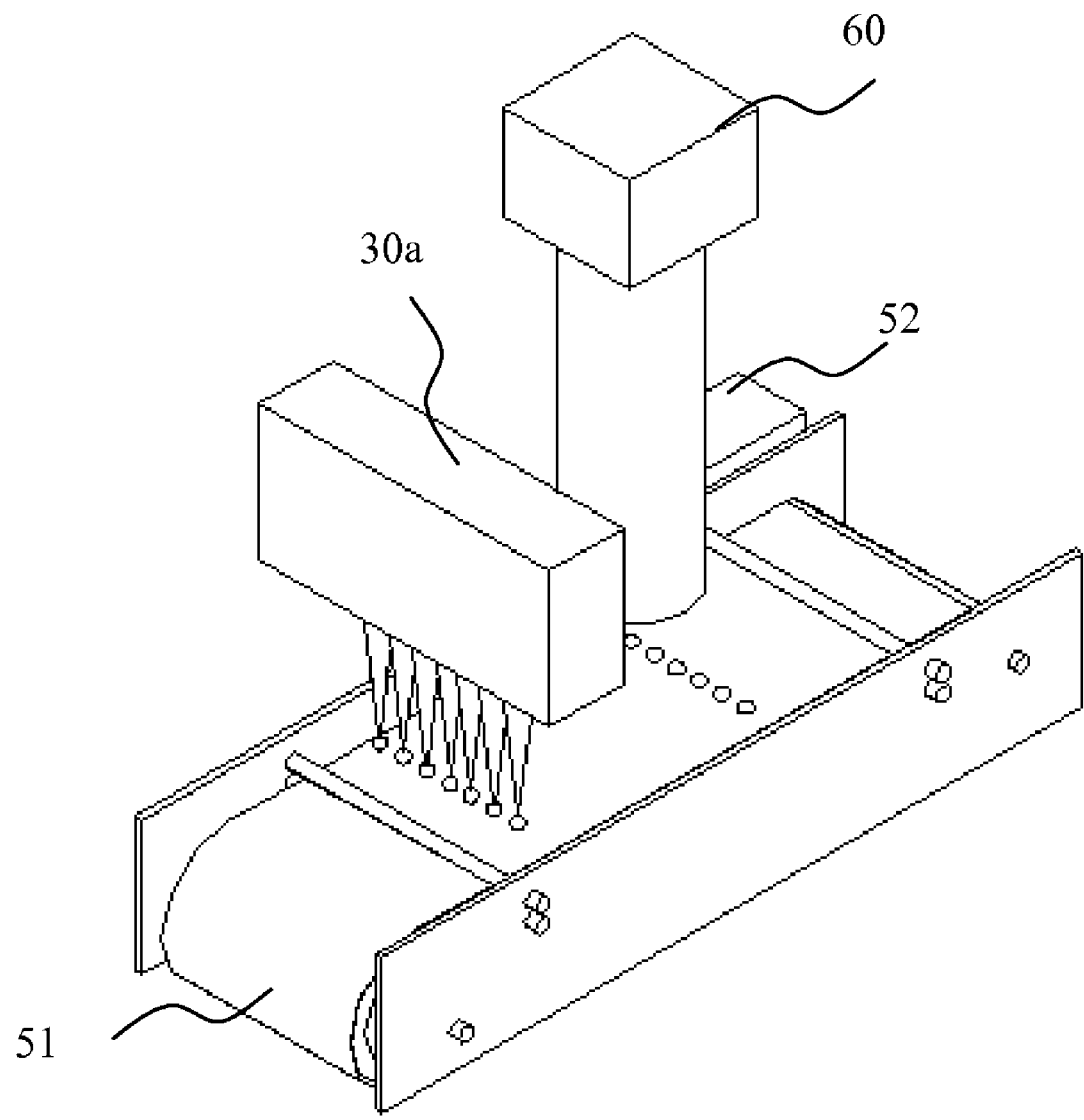

FIG. 5 shows yet another preferred embodiment of the present invention in which a pipette 30a is equipped with a multi-tip to allow multi-channel deposition of the solution onto a film or a deposition plate.

This embodiment allows further increase in productivity of testing of a large number of samples.

DETAILED DESCRIPTION OF THE SIXTH PREFERRED EMBODIMENT OF THE INVENTION

Figure 6:
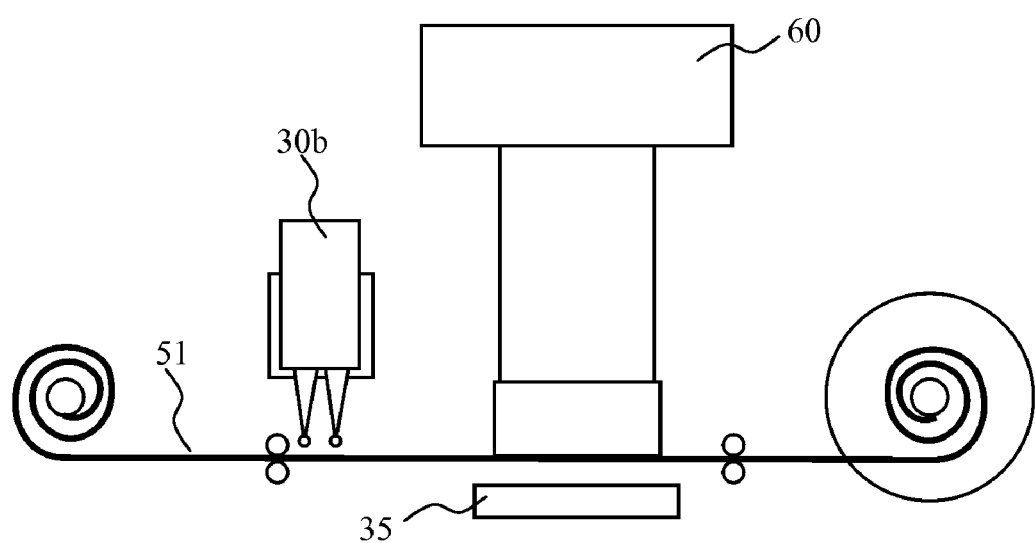

FIG. 6 shows a further yet embodiment of the present invention including a pipette 30b having multi-channel capability in the direction of film advancement. The drawing shows a two-channel pipette capable of depositing two droplets one close to another so that further processing and data collection can be done with two samples at a time rather than just one.

Of course, those skilled in the art would readily understand that two types of pipettes described for the fifth and sixth embodiments may be combined in such a way that more than one droplets is deposited in both directions—along and across the deposition plate or film.

DETAILED DESCRIPTION OF THE SEVENTH PREFERRED EMBODIMENT OF THE INVENTION

Figure 7:
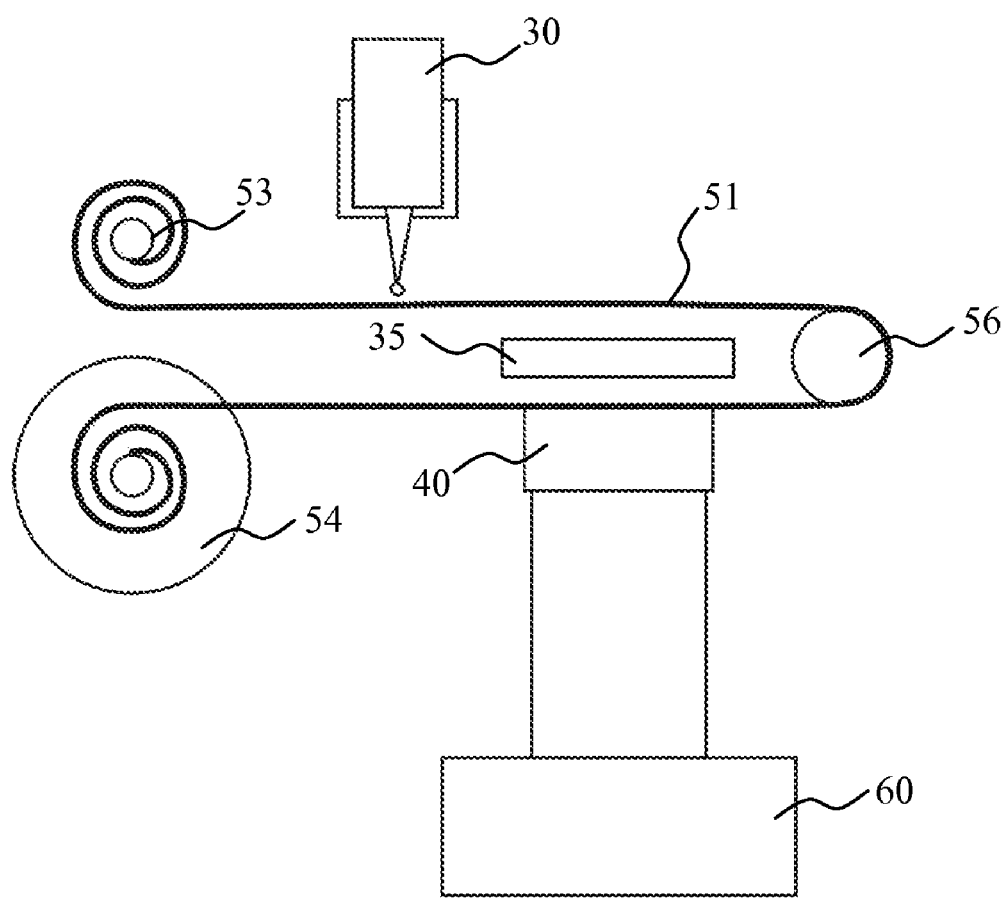
Figure 8:
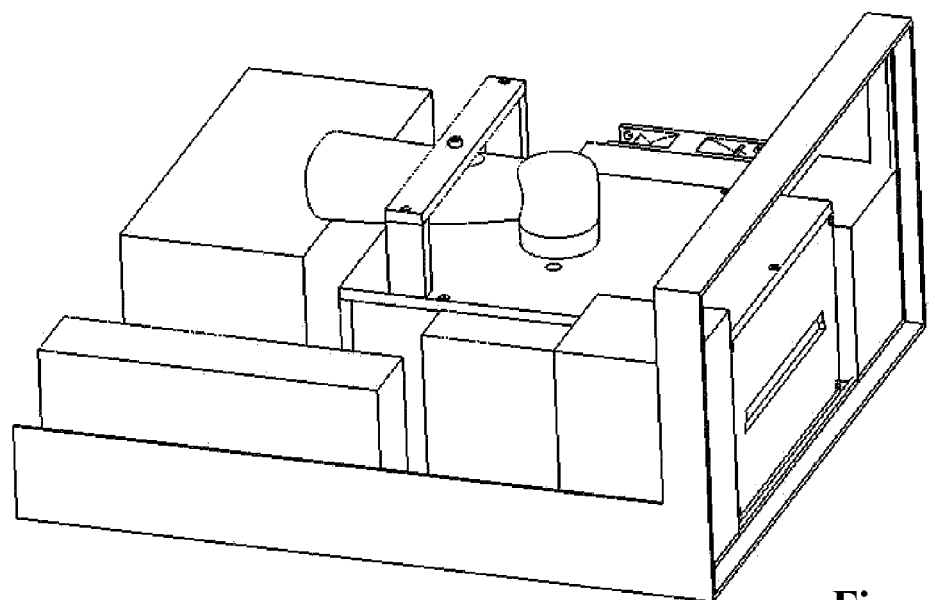
Figure 9:
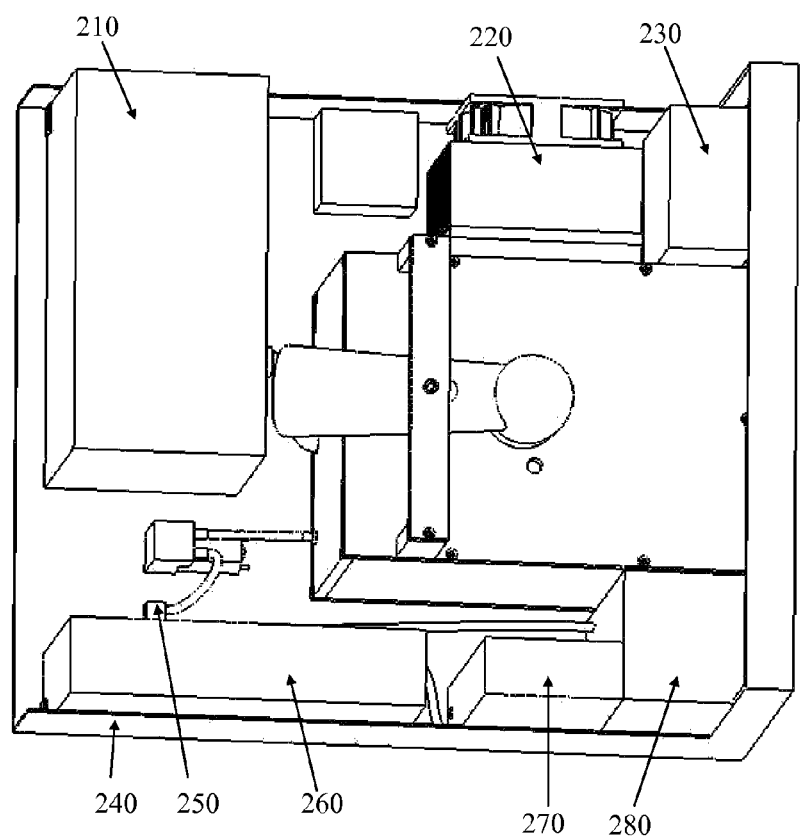

FIG. 7 shows another preferred embodiment of the invention in which the droplet deposition plate is inverted upside down so that the optical recording means are allowed to record the drying of the droplet in this inverted orientation. The deposition film 51 is rolled off the first roller 53 and the droplet of a solution is deposited thereon from a pipette 30. The film is then inverted about the roller 56 and the optical recording means 60 are mounted below and used to view, record and transmit data about the sample drying in this position.

DETAILED DESCRIPTION OF THE EIGHTH PREFERRED EMBODIMENT OF THE INVENTION

The main objective of the eighth and most preferred embodiment of the present invention is to build a DMC device with a sample carrier based on a modified compact disk (CD) drive, wherein the droplets will be deposited on a specially designed disposable CD-like disk with sections of coated and uncoated surfaces. The device is illustrated on FIGS. 8-11 and comprises four main subsystems that will (1) dispense the sample, (2) move it into position for data collection, (3) record the droplet drying, and (4) control the environment in the measuring chamber.

The subsystems will be controlled and coordinated by the user through a computer with software designed to conduct the experiment and store and analyze the data.

The design is based on a slightly modified standard CD drive. Modern CD drives represent a widely deployed, mature technology, and are thus reliable and inexpensive. All of the mechanical aspects of the design have been thoroughly developed and field tested. The mechanism for automatic insertion and ejection of the polycarbonate compact disks is gentle and robust. The high speeds of rotation of the disks necessary to achieve the reading rates of modern CD drives mean that the disk rotation mechanism must be exceptionally well balanced for such an inexpensive item. With the substitution of a stepper motor for slow positioning of the disk to align the samples with the light source and camera, the device takes advantage of the disk handling mechanism of the CD drive for the DMC device.

The major innovation of this particular embodiment of the invention concerns the slide carrier, which will be made in the form of a disposable CD-like disk. The use of transparent or nontransparent slides (or both) is contemplated for this invention allowing illumination from above or below the sample. Therefore two types of CD-like disks can be used: a standard polycarbonate disk with small glass (coated and non-coated) slides glued to the disk surface, and a disk with holes, in which slides are embedded in the form of small glass windows. In the simplest form of the device, slides are mounted on the disk circumferentially, all on one constant radius. It that case, up to about 100 slides can fit on one disposable CD-like disk. In a somewhat more complex mechanical system, the entire surface of the disk is used allowing for up to 1,000 slides to be located on one disk. There is a possibility that for certain applications, it will be feasible to make disks from a material that itself serves as a good deposition surface. In that case, the manufacturing of disks for the DMC device will be greatly simplified.

Gold-coated glass, mica and silicon wafers are readily available commercially but expensive. However, the technology developed for audio CDs may provide a low cost alternative. Audio CDs are produced beginning with injection molded polycarbonate disks. These disks are metallized by sputter coating or by vapor deposition; then a protective lacquer coating is applied. Typically, the metal coating is aluminum; however, gold also is used. Absent the outer lacquer layer, gold-coated polycarbonate disks may present an ideal format for the DMC CDs. The technology for producing them at low cost is highly developed. Self assembled monolayers could be created on the gold surface. If antibodies or other specific binding agents are to be immobilized, each can be sequestered to a particular region of the surface of the CD.

The slides on the disk could be coated with different reagents for more comprehensive characterization of the composition of the fluid. Since every disk will have a landmark enabling the computer to find any particular coating according a program defined by the user, one disk can be used for monitoring several diseases, for example by having such reagents as antibodies on its coated surfaces. Antibodies selected to detect particular proteins are preferred for the purpose of this invention.

Another possibility is to have different disposable disks optimized for a particular disease or a particular fluid (blood serum, urine, saliva, etc.). The disks will be inexpensive and cab be disposed of through normal medical waste channels.

There is a wide variety of possible substrates that could be used to produce uncoated or coated slides for DMC. Transparent materials such as glass, quartz, or polycarbonate may be used. Each of these materials can be coated. Particularly for glass and quartz, there are many options for directly attaching many chemical functionalities and macromolecules including proteins.

The optical system of the device comprises a digital microscope 290 and a fiber optic light source 210 with ring light attachment 320. Simple modifications to the optical system will permit monitoring of the position of fluorescent probes within the drying droplet. Using bandpass optical filters and/or colored LEDs inside this light source provides a possibility to illuminate the sample with light of a narrow band of wavelength for excitation of the fluorophore. Inclusion of an appropriate longpass filter between the sample and the microscope will block light within the incident wavelength band, yet allow passage of the light emitted from the fluorophore. A similar arrangement can be made for illumination of the sample from above.

The climate control system in the device includes temperature control and a humidity control means. The temperature in the measuring chamber is measured by a temperature sensor and controlled by the controller 230 using a thermoelectric module of the heat exchanger 220. The humidity is measured by the appropriate sensor. If measured humidity deviates from the set value, airflow is initiated from either a dehumidifier 270 or a humidifier 280. The airflow is controlled by the computer, which switches the pump 260 and fan and also controls the direction of the humidity change using a solenoid valve 250. There is no airflow during the measurement, unless needed to modify the desiccation rate at a certain stage of droplet drying. Using this arrangement, humidity and temperature control can be achieved with a precision of up to 0.5 degrees C. and 3% humidity, which is more than adequate for consistent desiccation conditions.

The device further uses a power supply 240 to provide energy to all components thereof.

In one version of the device, the droplet deposition system will include a fixed volume pipette and a tip holder-guide mounted on the panel of the measuring chamber. The operator will fill a disposable pipette tip with the sample, and mount the pipette on the device with the tip securely fixed into position by the tip holder-guide. Inside the measuring chamber, the disk will be aligned. This configuration will provide accuracy of droplet deposition location on the droplet deposition disk of about 0.1 mm, which meets the requirements for this procedure. After depositing the droplet on the disk, the stepper motor 13 will turn the disk and bring the deposited droplet into the field of view of the microscope 9.

In use, with the exception of loading of the disk and the sample, the DMC data collection and analysis will be automatic and transparent to the user. The user will select a disposable disk 300 based on the test to be performed and insert it into the device. Upon detecting disk insertion, the computer will find the home position of the disk 300. The computer will identify the disk type and serial number. The computer will set the environmental conditions in the measuring chamber appropriate for the test to be conducted. The user will be prompted to enter sample identifying information into the computer. Initially this will be done manually; however, addition of a bar code reader or similar automatic data entry device would be a further simple to implement improvement. The user will be instructed to fill and mount the dispensing pipette. The disk will be positioned for dispensing of a droplet onto a coated or uncoated segment thereof as appropriate. The user will be prompted to dispense the sample. The disk will be rotated to move the sample into the viewing location using a standard CD drive platform 310 and a motor 330. Images of the drying droplet sampled at about 2-3 second intervals provide sufficient time dependent data to follow the dynamics of droplet drying. Therefore there will be an ability to move the disk and/or optical components to view several droplets placed on the disk, which are drying simultaneously. Each droplet will be imaged in turn with a cycle time of 2-3 seconds. This ability will allow for fast comparison of a sample drying on multiple coatings under identical conditions all done within the time required for drying of a single droplet. The specific arrangement of the coatings on the disk depends on the number of desired coatings, the eventual ease of manufacture of the coated disk, the optical arrangement employed for viewing the disk and cost. Further improvements contemplated within the scope of this invention include concentric rings or wedges of different coatings.

The computer will begin recording the microscope output. The temperature and humidity in the sample chamber will be maintained or varied as appropriate for the test. Once the test is complete, as determined either by elapsed time or predetermined image criteria, data recording will be stopped. The data will be recorded and analyzed. After completion of the measurement, the user may be prompted for another test or the disk ejected for disposal.

Home-Use Applications

FIGS. 12 through 14 show the home-based version of the device designed for diagnostic purposes as well as remote monitoring of a patient in home settings. The general view of the device is shown on FIG. 12 and includes a pipette 130 along with a fluid collection container 131. The actual device consists of a housing 101 with an optional cover 102, which reveals a disposable droplet deposition slide 150 when open. The slide 150 is supplied from a side cartridge unit 120.

Further details of the device are revealed on FIG. 13 and include a optical recording and computer processor unit 160; climate control unit 140 allowing adjustments to the temperature and humidity of the droplet environment through a fan (not shown) drawing conditioned air from the chamber of the unit 140 and over the slide 150; automatic slide movement means 116 to draw the slide 150 into and out of the business end of the device; and the lighting means 135 to illuminate the droplet during its drying and image recording by the optical means 160. After the sequence of images of the process of drying is recorded, the slide 150 is automatically discarded into the bin 155. Conveniently, the unit 120 can be combined with the unit 155 to form a single use cartridge allowing several slides to be used and then discarded back therein so the user has to simply replace the entire assembly of both units once in a while.

The electrical diagram of the device and the details of its interaction via a wire or wireless connection with a remote data processing and analysis center such as at a hospital is shown on FIG. 14. Importantly, the procedure of use of the device is very simple and includes collecting of a sample of biological fluid by the patient into a fluid container 131 (such as saliva or urine for example); measuring the volume with pipette 130 and depositing the correct amount onto a slide 150. After that the rest of the process is fully automated and includes drawing of the slide 150 inside the device and activating of the process of drying the droplet and recording the sequence of images according to the methods described in more detail above. The information is then processed by the unit 160 and communicated to a remote location such as at the hospital via a built-in remote communication means.

One of the key features of the home-based version of the present invention is adaptive data processing, which enables the detection system to "learn" peculiarities of collected data sets for a particular person. Learning algorithms make it possible to significantly increase the sensitivity of present invention by fine tuning the device to specific features of a given subject. The learning ability of a home-use medical diagnostic system, such as home-use of the present invention, is based on the fact that the data collected during extended period of time provides means for defining much more precisely the "normal state" of an individual and thus, detecting meaningful deviations from the normal state with greater sensitivity.

Medical logic for diagnosis is typically based on the principle that healthy state of body is an objective notion and should be defined by "normal" range for certain parameters that are the same for a given population group. At the same time, it is well known that a notion of "normal" obtained on statistical basis can significantly differ from a "normal" value for a particular patient. For example, the pulse rate of 100 beats per minute could be normal for one person and extremely dangerous for another. Even for the same person, the measures normal in one condition can be hazardous in a different body state. In the home-use system a different principle can be implemented in which the ranges of parameters that define the healthy state are determined individually after collecting a sufficient body of data over an extended period of time.

Image Analysis

Once the optical data is collected, it is then processed to obtain the test results. Analysis of changes in the pattern parameters over time within a relatively small window (portion of the image) is the key element used for the image analysis according to the methods of the present invention. The selection of the set of analyzed pattern parameters is based on commonly accepted advanced image recognition techniques and includes:

Visualization of image data with scattergrams, histograms, line profiles and time-space plots;

Building time-dependent functions of image intensity such as average, mean standard deviation, max/min intensity ratio, and their derivatives and combinations for the same sample window and for the different sample windows;

Building shape and texture related functions of the image such as roughness, calculated fractal dimension of the image, border-related integrals of the image, mean direction angle, and their derivatives and combinations for the same sample window and for the different sample windows.

Pattern parameters are calculated for every selected examination window. The position of the examination window along the radius of the droplet may dramatically influence the time dependence of the parameter reflecting the fact that each such window characterizes a different fraction of molecular components of the sample, as it is illustrated in FIG. 15. Structural features appear distinctly different at different distances from the droplet center because of a radial distribution of the droplet's components.

In the example of image processing shown on FIG. 15, two windows are designated, one showed in solid line and the other shown in dotted line. The size and location of both windows is maintained the same throughout the sequence of analyzed images. A pattern parameter is then selected such as intensity in this particular example. The parameter is measured in the entire sequence of images and plotted as shown on the lower portion of FIG. 15. The graph has a solid line representing the change of the intensity for the solid line window and a dotted line representing the change of intensity for the dashed line window. The time scale is measured in number of images. One can observe the critical time difference in the peaks of intensities as well as the overall nature of the curves as recorded for each window. This shows that the analysis allows understanding various molecular components of the sample solution as they dry at different times and with different characteristics on the image of the drying droplet. Parallel analysis of patterns in two or more windows as appropriate for a given solution along the droplet radius will show changes of relative concentration of different components of the sample solution.

Characteristic features of calculated temporal dependences of image parameters in the selected window, such as position and amplitude of maxima and minima, position and slope of the inflection points, can be used for quantitative assessment of the tested sample.

The selection of the size of the sample windows is also important, as it is illustrated in FIG. 16. In the example of a drying droplet shown here, a smaller window (solid lines) produces a intensity derivative graph shown on the right portion of the figure, which is markedly different from the dotted line graph obtained from a larger window shown in dotted lines on the left. Although the location of the center of each window is the same, the size of the window makes a difference in the obtained result.

A smaller window provides more detailed information on temporal and spatial processes in the sediment formation but at the same time a decrease of the number of pixels in the analyzed pattern results in a poorer signal-to-noise ratio. Optimization of the window for analysis of a particular disease should be the first step in applying this type of technique of the drying droplet pattern assessment.

Data Processing

The source of information is a sequence of images of a droplet pattern recorded as separate images or as an integrated data file in AVI or MPEG format. The image resolution normally is 600×800 pixels with 24 bit color, but the resolution could be higher and a gray color palette also could be used. The actual format of the data, as well as the image color and resolution, depends on the camera and digital media used. The number of images may be several hundred or even several thousand. The software will preferably execute a multi-scale pass through the image sequence starting with a large step. For example, analyzing every $100^{th}$ image to check for changes in the selected pattern parameter will allow discarding ranges of images with small variations of this parameter. The ranges with essential variations are then passed through again with smaller step. The procedure is repeated until the kernel of the change is localized with the desired accuracy.

The image processing may be done after all data is collected. However, in a preferred embodiment, the data is analyzed, as it becomes available so that only useful information is recorded while other data is discarded. Another advantage of "live" analysis is the ability to detect the end of the drying cycle and advance the system to the next droplet to be analyzed without waiting for the expiration of a preset time delay.

In a variation of the method of the invention, a plurality of windows is selected on each image and at least one pattern parameter is calculated for each window. Analysis of changes of these parameters from one image to the next allows determining the distribution of changes of each parameter in time. That coupled with the known locations of the windows allows ultimately to determine both the temporal (time dependent) and geometrical (location on the image) distribution of changes of each parameter independently as well as a temporal and geometrical dynamics of changes of these parameters in comparison between themselves.

FIGS. 17 and 18 show an example of using DMC method for diagnosing a disease. Blood serum samples obtained from patients diagnosed with myeloma were evaluated. In parallel, healthy or "normal" donor blood samples were measured. FIG. 17 shows a typical example of data obtained from normal and myeloma samples. The total number of video frames recorded during droplet drying is 500 but only 3 representative snapshots are shown for each sample. The curves below the images illustrate the data analysis algorithm which consists of several distinct steps. The first step is to select an examination window—the particular part of the image for which temporal changes of structural parameters will be calculated. This selected examination window is shown in FIG. 17 as a square on the left side of each snapshot. The position of the examination window along the radius of the droplet may dramatically influence the time dependence of the parameter reflecting the fact that each such window characterizes a different fraction of molecular components of the sample. The following steps are related to feature extraction and selection. Because the recorded video is an extremely high-dimensionality data source, it is important to reduce the dimensionality by filtering and extracting the information most relevant to a particular objective. The DMC software calculates various pattern parameters as a function of time in the selected window. The left graphs under each row of images show the time dependence of just two parameters. One of the plotted parameters reflects intensity variation in the measuring window at any given moment of time, and the second one is related to the changes in contrast in the examination window. The next step in data analysis is to create a simple visual form ("the signature") for human viewing and distinguishing similar and differing samples. An example of such a signature is shown in the right graphs under each row of images. In this case, the signature represents the curve obtained by plotting the two parameters shown in the left graph against each other. As it is seen in FIG. 18, the obtained signatures are distinctly different and, most importantly, they are reproducible for each group of samples.

The hundreds of frames recorded during droplet drying provide a wealth of data on the process of temporal and spatial separation of molecular components of investigated fluid. In many cases even a small fraction of that rich information could be sufficient for reliable separation of different groups of samples. For example, only limited number of recorded frames related to the time interval when certain characteristic pattern feature is formed can be taken for the analysis. Ultimately, we may use only one of the images taken in the drying process and still be able to reliably separate groups of samples. FIG. 19 illustrates one such possibility. Only the final image of the dried droplet is used for the analysis. In that case, the chosen window is scanned along the radius of the image and the evolution of the pattern in space rather than in time is analyzed. The upper panel in FIG. 19 shows the final patterns of two dried droplets of the normal blood serum. The window for pattern analysis shown in the central part of each image is moved along the shown radius. The software calculates tens of pattern parameters within the chosen window as a function of its position during movement along the radius. The bottom left panel of FIG. 19 shows just two parameters one of which reflects intensity variation in the examination window and the second one is related to the changes in contrast in the window. Characteristic features of these curves, such as position and amplitude of maxima and minima, position and slope of the inflection points, can used for quantitative assessment of the tested sample. All these features of the curves reflect the composition of the droplet and dynamics of the sediment formation. In addition to that, the detailed shape of these curves is influenced by numerous "noise" factors such as variation of the droplet initial volume, ratio of its height to diameter, temperature and humidity in the measuring chamber. One of the preferred ways of improving the signal-to-noise ratio in the information provided by these calculated curves is to relate the change in a parameter of the pattern to a different parameter within the same window. Plotting the changes of one parameter against respective change in a different parameter greatly reduces the noise caused by variations of droplet size and the desiccation rate. Graphs shown in the bottom right panels of FIG. 19 (D and E) and denoted as $A_s$ and $B_s$, where the subscript S stands for "Signature", represent such plots. These graphs represent a simple visual form ("the signature") for human viewing and distinguishing similar and differing samples. At the same time, characteristic graphical features of the signature can be used for quantitative assessment of the samples. The signatures shown in FIG. 19 characterizing two normal blood serum samples A and B have numerous similar geometrical features.

Various means are contemplated to enhance the sensitivity of the methods of the present invention in addition to the described above concept of coating the deposition means with a target agent compound to cause a reaction with a portion or the entire chemical structure of the droplet. One method of enhancement is generally referred to as "zooming". The essence of it is to slow down the rate of droplet drying by changing the humidity and temperature, when the concentration of certain critical components has reached a certain critical predetermined level. It is advantageous to slow down or even completely stop the drying process by increasing humidity or adding solvent to the droplet once the process of crystallization or another sharp structural transition has started or about to start so that more information can be extracted by the device of the invention from the process of drying of the droplet. More than one zooming can be used for analysis of a droplet having a complicated structure.

Another method to further extend the sensitivity of the method and the device of the present invention is to use so-called "pattering" of the coatings for the purposes of the deposition surface of the deposition means of the invention. Specifically, the coating over the surface of a deposition means may be done in a series of geometrical shapes such as squares, lines or other patterns rather than coating the entire surface so as to change advantageously the process of drying of the droplet. Patterning with biological ligands coatings or nucleation centers can be used advantageously for this purpose. Such patterning can further increase the sensitivity by influencing the process of crystallization especially if it is optionally combined with application of a target agent compound to the surface of the deposition means to induce different crystallization kinetics or geometry.

Yet another method to further extend the sensitivity of the method of the present invention is to use various types of illumination of the drying droplet so that the device of the invention can better detect some particular aspects of crystallization. Specifically, visible, polarized, IR, fluorescent, or UV light can be used separately or in combination for illumination of the droplet as well as a light of a certain predetermined wavelength or a range of wavelengths.

Of course, all of the above methods of enhancing the sensitivity of the analysis may be deployed separately or in combination with other methods.

Although the invention herein has been described with respect to particular embodiments, it is understood that these embodiments are merely illustrative of the principles and applications of the present invention. For example, if the devices and methods of the invention are used with biological fluids, a variety of medical conditions and diseases may be rapidly identified. It is therefore to be understood that numerous modifications may be made to the illustrative embodiments and that other arrangements may be devised without departing from the spirit and scope of the present invention as defined by the appended claims.

I claim:

1. A method for evaluating dynamics of incremental changes in a sedimentary pattern formed by a droplet of a solution, said method comprising the steps of:
    a) depositing said droplet on a surface of a droplet deposition means, said surface including a coating to alter the process of sedimentation of said solution on said droplet deposition means,
    b) recording a sequence of images of the sedimentary patterns formed during drying of said droplet, said images covering the entire droplet,
    c) selecting a plurality of windows within each image, each window having a predetermined size and shape within each image at a constant location throughout the recorded sequence of images, said windows radially distributed from the center of said droplet towards its periphery,
    d) calculating at least one predetermined pattern parameter in each window for each of said successive images, and
    e) analyzing changes of said parameter in said plurality of windows from one image to the next as a function of time and the respective location of the windows on said image.

2. The method as in claim 1, wherein said droplet deposition means include a plurality of individual surfaces, each of said surfaces coated with a corresponding coating compound to selectively interact with certain components of said solution, said step (a) including depositing a plurality of droplets of said solution over said surfaces such that individual droplets are deposited over said individual surfaces, whereby said coating compounds individually and selectively altering the drying process dynamics of said solution when said components are present therein therefore differentially enhancing detection of presence of said components in said solution if such alteration of drying process dynamics is detected.

3. The method as in claim 2, wherein said coatings include antibodies.

4. The method as in claim 3, wherein said antibodies are selected to react with predetermined proteins, whereby allowing detection of said proteins in said solution.

5. The method as in claim 1, wherein said coating compound is applied to said surface of said droplet deposition means in a predetermined geometrical pattern adapted to be covered entirely by said droplet so as to further alter the process of sediment formation during the drying of said droplet.

* * * * *